(12) United States Patent
Cheng et al.

(10) Patent No.: US 12,227,736 B2
(45) Date of Patent: Feb. 18, 2025

(54) *STENOTROPHOMONAS MALTOPHILIA* GYH AND APPLICATION THEREOF IN DEGRADATION OF CHLORINATED HYDROCARBON POLLUTANTS

(71) Applicant: Zhejiang University of Technology, Zhejiang (CN)

(72) Inventors: Zhuowei Cheng, Zhejiang (CN); Dongzhi Chen, Zhejiang (CN); Jiade Wang, Zhejiang (CN); Jianming Yu, Zhejiang (CN); Jianmeng Chen, Zhejiang (CN); Yanhong Guan, Zhejiang (CN)

(73) Assignee: ZHEJIANG UNIVERSITY OF TECHNOLOGY, Zhejiang (CN)

( * ) Notice: Subject to any disclaimer, the term of this patent is extended or adjusted under 35 U.S.C. 154(b) by 250 days.

(21) Appl. No.: 17/632,977

(22) PCT Filed: Jul. 31, 2020

(86) PCT No.: PCT/CN2020/106155
§ 371 (c)(1),
(2) Date: Feb. 4, 2022

(87) PCT Pub. No.: WO2021/147293
PCT Pub. Date: Jul. 29, 2021

(65) Prior Publication Data
US 2022/0275324 A1    Sep. 1, 2022

(30) Foreign Application Priority Data
Jan. 20, 2020    (CN) .......................... 202010062189.2

(51) Int. Cl.
*C12N 1/20*    (2006.01)
*A62D 101/22*   (2007.01)
*C12R 1/01*    (2006.01)

(52) U.S. Cl.
CPC .......... *C12N 1/205* (2021.05); *A62D 2101/22* (2013.01); *C12R 2001/01* (2021.05)

(58) Field of Classification Search
CPC ...... C12N 1/205; C12N 1/20; A62D 2101/22; A62D 3/02; C12R 2001/01; C02F 3/341; C02F 2101/32; C02F 2101/36
See application file for complete search history.

(56) References Cited

FOREIGN PATENT DOCUMENTS

| CN | 105820978 A | 8/2016 |
| CN | 111254091 A | 6/2020 |
| WO | WO-0063527 A1 | 10/2000 |

OTHER PUBLICATIONS

Brooke JS, Stenotrophomonas maltophilia: an Emerging Global Opportunistic Pathogen, 2012, Clin Microbiol Rev, 25:2-41, https://doi.org/10.1128/cmr.00019-11 (Year: 2012).*

Zhou. Ting et al.; "Repair Effect of Stenotrophomonas Maltophilia J03 on Quinclorac-Injured Flue-Cured Tobacco"; Acta Tabacaria Sinica; Aug. 27, 2019; pp. 86-90; vol. 25. No. 5.

Mukherjee, Pet al.; "Persistent Organic Pollutants Induced Protein Expression and Immunocrossreactivity by Stenotrophomonas maltophilia PM102: A Prospective Bioremediating Candidate"; Biomed Research International; Jun. 26, 2013; pp. 1-8; vol. 2013.

* cited by examiner

*Primary Examiner* — Louise W Humphrey
*Assistant Examiner* — Anjali Ajit Hirani
(74) *Attorney, Agent, or Firm* — MUNCY, GEISSLER, OLDS & LOWE. P.C.

(57) ABSTRACT

The present invention discloses *Stenotrophomonas maltophilia* GYH and its application in degrading chlorinated hydrocarbon pollutants, and the application is carried out as follows: resting cells obtained by spreading cultivation of *Stenotrophomonas maltophilia* GYH are added to a pH=5-8 inorganic salt medium, and then a chlorinated hydrocarbon pollutant is added, and the cells are cultured at 20-35° C. and 140-180 rpm to degrade the pollutant. The concentration of chlorinated hydrocarbon pollutant which can be removed by *Stenotrophomonas maltophilia* GYH ranges from 2.9 mg/L to 8.93 mg/L. Therefore, the *Stenotrophomonas maltophilia* has a highly efficient degradation ability for similar industrial pollutants and is able to withstand high concentrations of these pollutants.

6 Claims, 6 Drawing Sheets

Specification includes a Sequence Listing.

STENOTROPHOMONAS MALTOPHILIA GYH AND APPLICATION THEREOF IN DEGRADATION OF CHLORINATED HYDROCARBON POLLUTANTS

TECHNICAL FIELD

The present invention relates to *Stenotrophomonas maltophilia* GYH and its application in degradation of pollutants such as chloroform.

BACKGROUND ART

A chlorinated hydrocarbon is a halogenated hydrocarbon formed by substituting hydrogen atom(s) in a hydrocarbon molecule with chlorine atom(s). Halogenated hydrocarbons are classified into fluorinated hydrocarbons, chlorinated hydrocarbons, brominated hydrocarbons and iodinated hydrocarbons according to the halogens substituted; they can also be classified into monohalogenated hydrocarbons, dihalogenated hydrocarbons and polyhalogenated hydrocarbons according to the number of halogen atoms in the molecule. Lower hydrocarbon is gas or liquid, and higher hydrocarbon is solid. Most halogenated hydrocarbons are insoluble or slightly soluble in water, but soluble in organic solvents. Most halogenated hydrocarbons have a special odor. Halogenated hydrocarbons are an important type of organic synthetic intermediates and raw materials for many organic synthesis. Many halogenated hydrocarbons can be used as fire extinguishing agents (e.g., carbon tetrachloride), refrigerants (e.g., freon), and anesthetics (e.g., chloroform, which is not currently unused), insecticides (e.g., hexachloro-cyclohexane, which is currently banned), raw materials for the polymer industry (e.g., vinyl chloride, tetrafluoroethylene), and the important halogenated hydrocarbons-freon. Halogens are highly toxic groups, and halogenated hydrocarbons are generally more toxic than their parent hydrocarbons. After being absorbed by the skin, the halogenated hydrocarbon invades the nerve center or acts on the internal organs, causing poisoning. Generally, iodinated hydrocarbons are the most toxic, while brominated hydrocarbons, chlorinated hydrocarbons and fluorinated hydrocarbons are successively less toxic. Lower halogenated hydrocarbons are more toxic than higher halogenated hydrocarbons; saturated halogenated hydrocarbons are more toxic than unsaturated halogenated hydrocarbons; polyhalogenated hydrocarbons are more toxic than halogenated hydrocarbons with less halogen.

Trichloromethane is mainly used to produce freon, dye and medicine, is commonly used as an anesthetic in medicine, and can be used as a solvent and extractant for antibiotics, spices, grease, resin and rubber. It can be mixed with tetrachloromethane to make non-freezing fireproof liquid, and it can also be used as aerosol propellant, grain fumigant and standard liquid for calibrating temperature. Trichloromethane mainly acts on the central nervous system, has an anesthetic effect and does harm to heart, liver, and kidney. When inhaling it or absorbing it through the skin causes acute poisoning, the early symptoms, such as headache, dizziness, nausea, vomiting, excitement, hot and humid skin and mucous membrane irritation and the late symptoms, such as mental disorder, superficial respiratory syndrome, disappearance of reflexes, coma and even more seriously, respiratory paralysis and ventricular fibrillation will appear. And the late symptoms may also be accompanied by liver and kidney damage. When accidentally poisoning, there will be stomach burns with nausea, vomiting, abdominal pain and diarrhea, followed by symptoms of anesthesia. The liquid can cause dermatitis, eczema and even skin burn. The chronic effects mainly cause liver damage, and have symptoms such as dyspepsia, asthenia, headache, insomnia and the like, and a few patients have kidney damage and chloroform addiction.

Therefore, it is necessary to study the degradation of chloroform in the environment for human health. Through literature search, there are some reports on the biodegradation of polycyclic aromatic hydrocarbons, benzopyrene, and cyclotrimethylene trinitramine by *Stenotrophomonas maltophilia*, but no report that *Stenotrophomonas maltophilia* uses chloroform and the like as the only carbon source to achieve high-efficient degradation has been found. *Stenotrophomonas maltophilia* GYH of the present invention can use chloroform and the like as the only carbon source to achieve degradation, the growth environment is mild and it is easy to carry out large-scale cultivation. The discovery of the degrading bacteria is of great significance for high-efficient purification of chlorinated hydrocarbon pollutants in industrial wastewater and exhaust gas.

SUMMARY OF THE INVENTION

The object of the present invention is to provide *Stenotrophomonas maltophilia* and its application in degrading chlorinated hydrocarbon pollutants, and the strain has high efficiency in removing pollutants.

The present invention adopts the technical solution as follows:

The present invention provides a new strain—*Stenotrophomonas maltophilia* GYH, which is preserved in China Center for Type Culture Collection, the preservation number is CCTCC NO: M 20191025, the preservation date is Dec. 9, 2019, and the preservation address is Wuhan University, Wuhan, China, 430072.

The basic characteristics of the *Stenotrophomonas maltophilia* GYH of the present invention are as follows: the colonies are pale yellow in color, opaque, smooth and moist, and easy to pick, and their edges are neat. Under the transmission electron microscope, morphology of the bacteria cell is ellipsoidal, with flagella, and Gram-negative.

The present invention also provides an application of *Stenotrophomonas maltophilia* GYH in degrading a chlorinated hydrocarbon pollutant, and the application is specifically as follows: resting cells obtained by spreading cultivation of *Stenotrophomonas maltophilia* GYH are added to a pH=5-8 (preferably pH=7) inorganic salt medium, and then the chlorinated hydrocarbon pollutant is added, and the cells are cultured at 20-35° C. and 140-180 rpm (preferably at 30° C., 160 rpm) to degrade the pollutant.

Further, the chlorinated hydrocarbon pollutant is at least one selected from the group consisting of chloroform, chlorobenzene, 1,2-dichloroethane, 1,1,1-trichloroethane and dichloromethane.

Further, in the inorganic salt medium, the amount of the resting cells calculated by the dry weight of the bacteria is 50-100 mg/L preferably is 80 mg/L.

Further, the initial concentration of the chlorinated hydrocarbon pollutant in the inorganic salt medium is 1-10 mg/L, preferably is 2.98-8.93 mg/L.

Further, the composition of the inorganic salt medium is as follows: $KH_2PO_4$ 2 g/L, $(NH_4)_2SO_4$ 2 g/L, $MgSO_4$ 0.025 g/L and NaOH 0.18 g/L, the solvent is ultrapure water, pH 5-8.

In the present invention, *Stenotrophomonas maltophilia* GYH is inoculated into LB liquid medium and incubated at 30° C. and 160 rpm for 2 days to activate and recover the stored bacteria, and then the activated bacteria are streaked on an LB agar medium and incubated at 30° C. in an incubator, the resulting single colonies are picked out and streaked on a plate to examine their purification, thereby obtaining a bacterial slant which can be maintained routinely (4° C.) and needs to be transferred every three months to ensure the activity of the bacteria.

Further, the resting cells of *Stenotrophomonas maltophilia* GYH are prepared as follows:

(1) Slant Incubation:

*Stenotrophomonas maltophilia* GYH is inoculated onto LB agar medium and cultivated at 30° C. in an incubator, thereby obtaining a bacterial slant wherein the LB agar medium composition is as follows: 5 g/L yeast extract, 10 g/L $NaNO_3$, 10 g/L peptone, 15-20 g/L agar, natural pH, deionized water as solvent;

(2) Spreading Cultivation the slant cells in step (1) are inoculated into LB liquid medium and incubated at 30° C., 160 rpm for 12 h, then the obtained spreading cultivation solution is centrifuged to collect wet cells, and the wet cells are washed with inorganic salt medium to obtain the resting cells of *Stenotrophomonas maltophilia* GYH; wherein the LB liquid medium composition is as follows: 5 g/L yeast extract, 10 g/L $NaNO_3$, 10 g/L peptone, deionized water as solvent, natural pH.

Compared with prior art, advantages of the present invention are embodied in:

*Stenotrophomonas maltophilia* GYH of the present invention is taken from sludge in a sewage plant and has a good degradation effect on chlorinated hydrocarbons, especially chloroform, which can be converted into harmless substances such as $CO_2$, $H_2O$, etc.

The concentration of chlorinated hydrocarbon pollutants which can be removed by *Stenotrophomonas maltophilia* GYH ranges from 2.9 mg/L to 8.93 mg/L. Therefore, the *Stenotrophomonas maltophilia* has a highly efficient degradation ability for similar industrial pollutants (such as chlorobenzene, etc.) and is able to withstand high concentrations of these pollutants.

SPECIFIC EMBODIMENTS

The present invention is further illustrated below with specific examples, but the scope of the present invention is not limited thereto:

The materials and reagents used in the following examples can be obtained from commercial sources unless otherwise specified.

Example 1: Isolation, Purification and Identification of *Stenotrophomonas maltophilia* GYH 1. Isolation and Purification of *Stenotrophomonas maltophilia* GYH

Figure 1:
FIG. 1 is a colony morphology image of the strain GYH on LB medium.
Figure 2:
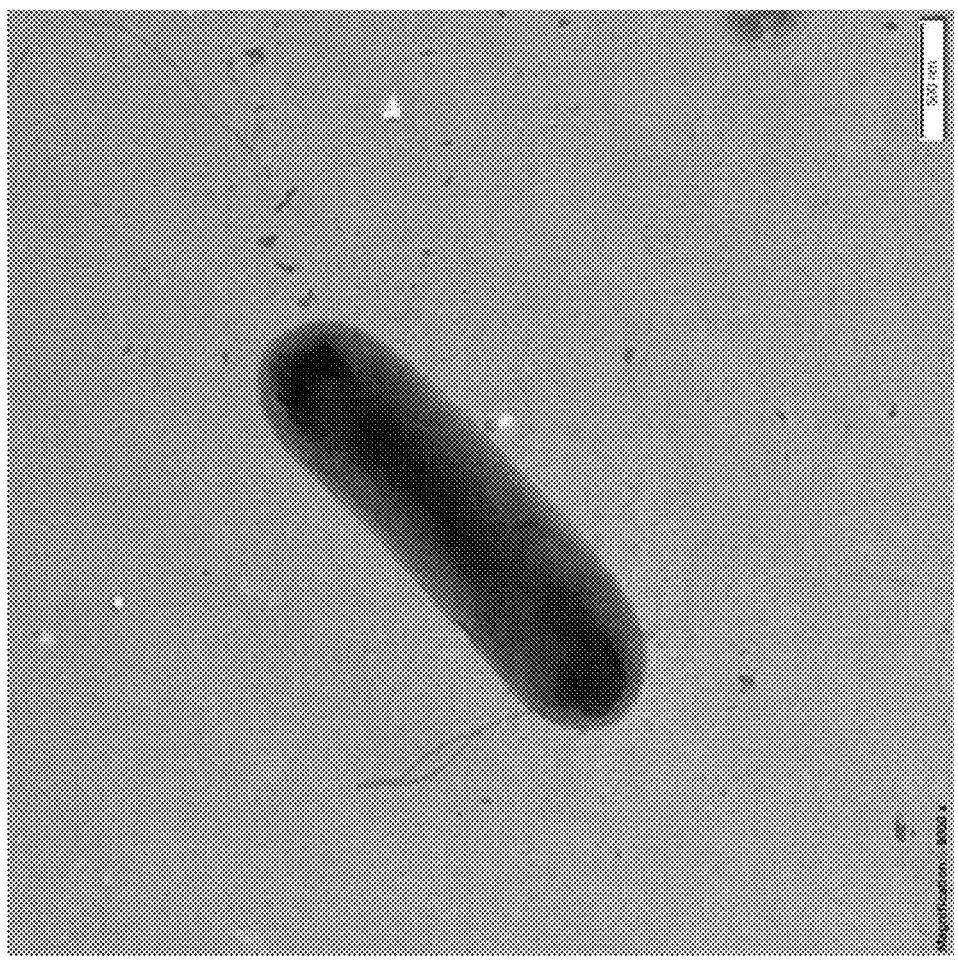
FIG. 2 is a transmission electron microscopy image of the strain GYH.

*Stenotrophomonas maltophilia* GYH is Gram-negative bacteria domesticated and isolated from activated sludge. The specific steps are as follows:

50 mL of inorganic salt medium was added to a 300 mL shake flask, and 10 mL of activated sludge and 8.9 mg/L of chloroform were added for enrichment culture. When the concentration of chloroform reached 50% of the initial concentration, 5 mL of the enrichment solution was taken out and added to 50 ml of fresh inorganic salt medium and chloroform was added with a final concentration of 8.9 mg/L, after the above enrichment process had been repeated 5 times, the last enrichment solution was spread on LB agar medium after gradient dilution. A single colony was selected and inoculated to an isolation agar medium by streaking for purification (FIG. 1), the resulting colony was inoculated to inorganic salt medium, and chloroform was added as the only carbon source and energy with a final concentration of 8.9 mg/L for verification, thereby obtaining the target strain with chloroform degradation ability, which was denoted as strain GYH. Its morphology was identified by transmission electron microscope (FIG. 2).

The inorganic salt medium composition was as follows: $KH_2PO_4$ 2 g/L, $(NH_4)_2SO_4$ 2 g/L, $MgSO_4$ 0.025 g/L, NaOH 0.18 g/L, the solvent was ultrapure water, pH 5-8.

The LB agar medium composition was as follows: 5 g/L yeast extract, 10 g/L $NaNO_3$, 10 g/L peptone, 18 g/L agar, natural pH, and the solvent is deionized water.

The LB liquid medium composition was as follows: 5 g/L yeast extract, 10 g/L $NaNO_3$, 10 g/L peptone, natural pH, and the solvent is deionized water.

The isolation agar medium was prepared as follows: agar was added to inorganic salt medium with the final concentration of 18 g/L, thereby obtaining the isolation agar medium, and when the isolation agar medium was used, chloroform was added as a carbon source with the final concentration of 8.9 mg/L.

2. Identification of the Strain GYH (1) The Characteristics of the Strain GYH

The colonies were light yellow with neat edges, opaque, smooth, moist, and easy to pick. Under a transmission electron microscope, the bacteria were ellipsoidal, had flagella and a cell size of 655×2577 nm, and were Gram-negative. Through 16S rRNA sequence analysis and physiological and biochemical identification, the strain was determined to be *Stenotrophomonas maltophilia*. The specific steps were as follows:

(2) 16S rRNA Sequencing

Figure 3:
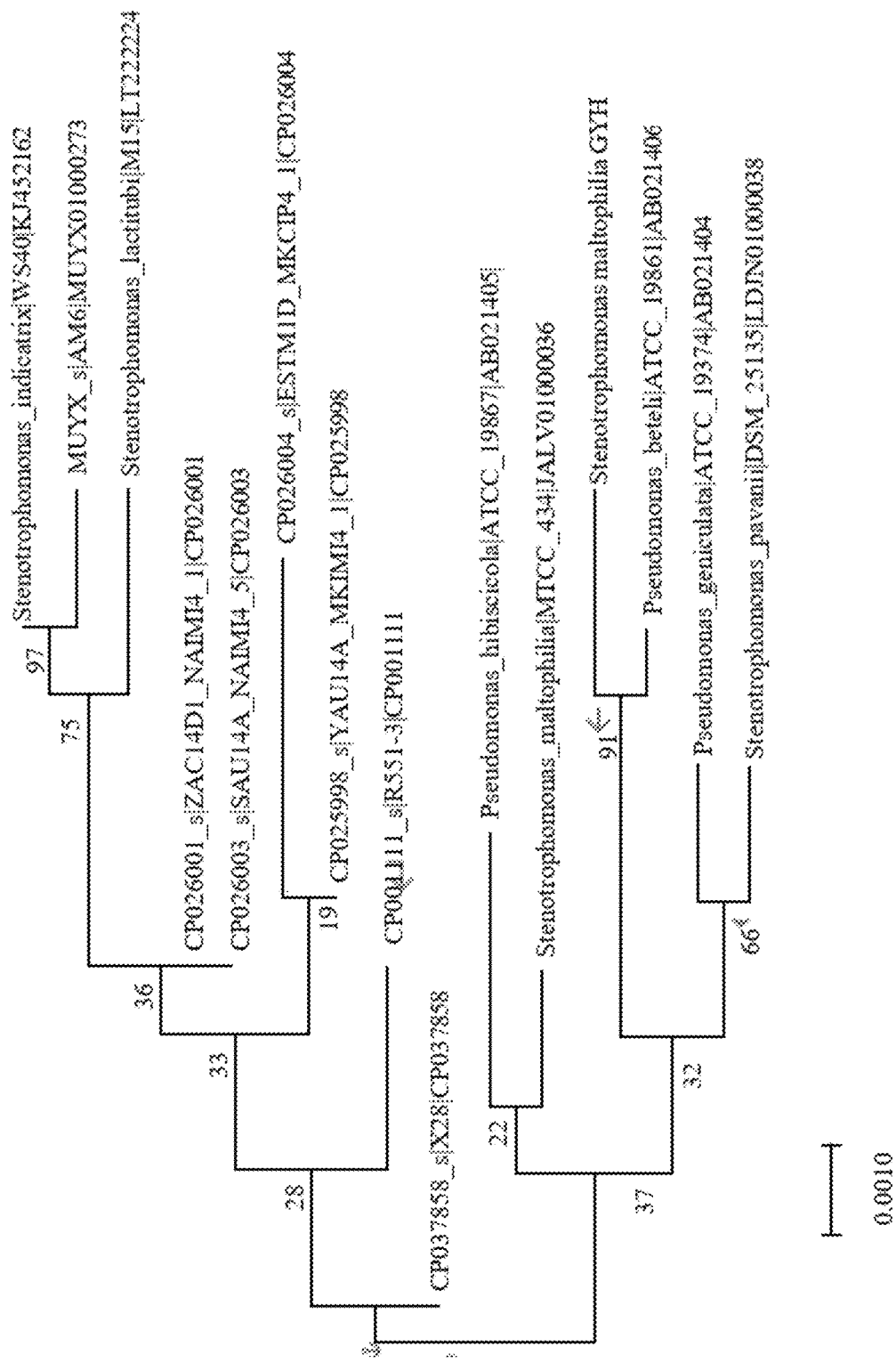
FIG. 3 is a dendrogram of the strain GYH.

The DNA of the strain GYH was extracted and purified using Ezup Column Bacteria Genomic DNA Purification Kit, and stored at 4° C. The purified DNA was amplified by PCR with bacterial universal primers which were 27F (AGAGTTTGATCCTGGCTCAG) and 1492 R (GGTTACCTTGTTACGACTT). The PCR reaction program was set as follows: pre-denaturation at 94° C. for 4 min, 30 cycles of denaturation at 94° C. for 45 s, annealing at 55° C. for 45 s and extension at 72° C. for 1 min, and finally extension at 72° C. for 10 min. The PCR product was purified and recovered for sequencing (Zhejiang Tianke High Technology Development Co. Ltd.). The sequence homology of the 16S rRNA sequencing result (the nucleotide sequence is shown in SEQ ID NO.1, it was uploaded to GenBank, thereby obtaining the NCBI gene accession No:

MN860228) and the gene sequences uploaded to Genbank was compared, it was found that it belonged to the genus *Stenotrophomonas* and had the highest homology with *Stenotrophomonas maltophilia*, reaching 99%. From the results, 15 representative strains of *Stenotrophomonas* were selected and a phylogenetic tree shown in FIG. 3 was constructed using MEGA7 software based on the sequence homology of their 16S rRNA genes.

(3) Utilization Ability of the Strain GYH on 63 Carbon Sources on Mérieux GN Card.

BioMérieux automated microbial analyzer was used to investigate metabolism of 63 different carbon sources by the strain (entrusted to Zhejiang Tianke High Technology Development Co. Ltd. (formerly Zhejiang Institute of Microbiology)). The identification results were shown in Table 1. According to the biochemical reaction of Bio-Mérieux automated microbial analyzer VITEK, the strain GYH can consume 11 kinds of carbon sources, but cannot consume the other 52 kinds of carbon sources.

TABLE 1

Biochemical reaction results of the strain GYH detected by BioMerieux automated microbial analyzer VITEK (GN card)

| Number | Abbreviation | Chinese name | Testing results |
|---|---|---|---|
| 2 | APPA | Ala-Phe-Pro-arylamidase | + |
| 3 | ADO | Adonitol | − |
| 4 | PyrA | L-Pyrrolydonyl-arylamidase | − |
| 5 | IARL | L-Arabitol | − |
| 7 | dCEL | D-cellobiose | − |
| 9 | BGAL | β-Galactosidase | − |
| 10 | H2S | H2S production | − |
| 11 | BNAG | β-N-Acetyl-glucosaminidase | − |
| 12 | AGLTp | Glutamyl arylamidase pNA | − |
| 13 | dGLU | D-Glucose | − |
| 14 | GGT | γ-Glutamyl-transferase | + |
| 15 | OFF | Fermentation/Glucose | − |
| 17 | BGLU | β-Glucosidase | + |
| 18 | dMAL | D-Maltose | − |
| 19 | dMAN | D-Mannitol | − |
| 20 | dMNE | D-Mannose | − |
| 21 | BXYL | β-Xylosidase | − |
| 22 | BAIap | β-Alanine Arylamidase pNA | − |
| 23 | ProA | L-Proline Arylamidase | + |
| 26 | LIP | Lipase | + |
| 27 | PLE | Palatinose | − |
| 29 | TyrA | Tyrosine Arylamidase | − |
| 31 | URE | Urease | − |
| 32 | dSOR | D-Sorbrtol | − |
| 33 | SAC | Sucrose | − |
| 34 | dTAG | D-Tagatose | − |
| 35 | dTRE | D-Trehalose | − |
| 36 | CIT | Citrate (sodium) | + |
| 37 | MNT | Malonate | − |
| 39 | 5KG | 5-Keto-D-gluconate | − |
| 40 | ILATk | L-Lactate alkalinisation | + |
| 41 | AGLU | α-Glucosidase | + |
| 42 | SUCT | Succinate alkalinisation | + |
| 43 | NAGA | β-N-Acetyl-galactosaminidase | − |
| 44 | AGAL | α-Galactosidase | − |
| 45 | PHOS | Phosphatase | + |
| 46 | GlyA | Glycine Arylamidase | − |
| 47 | ODC | Ornithine decarboxylase | − |
| 48 | LDC | Lysine decarboxylase | − |
| 53 | IHISa | L-Histidine assimilation | − |
| 56 | CMT | Coumarate | − |
| 57 | BGUR | β-Glucoronidase | − |
| 58 | O129R | O/129 Resistance (comp. vibrio.) | − |
| 59 | GGAA | Glu-Gly-Arg-arylamidase | + |
| 61 | IMLTa | L-Malate assimilation | − |
| 62 | ELLM | ELLMAN | − |
| 64 | ILATa | L-lactate assimilation | − |

Symbols:
+, positive;
−, negative

Through physiological and biochemical characteristics, genetic distance and comparison of 16S rRNA sequence, the strain GYH was identified as *Stenotrophomonas maltophilia*, named *Stenotrophamonas maltophilia* GYH, and stored in China Center for Type Collection, the preservation number is CCTCC NO: M20191025, and the preservation date is Dec. 9, 2019.

Example 2 Obtaining the Resting Cells of *Stenotrophomonas maltophilia*

1. Slant Cultivation:
*Stenotrophomonas maltophilia* CCTCC NO: M 20191025 was inoculated into LB liquid medium and incubated at 30° C., 160 rpm for 2 d, and then the activated bacteria were streaked on an LB agar plate and incubated at 30° C. in an incubator for 24 hours. The resulting single colonies were picked out, streaked on a plate to examine their purification, and stored on a slant of an LB test tube (4° C.).

2. Spreading Cultivation
The slant cells of step 1 were inoculated into LB liquid medium and incubated at 30° C. 160 rpm for 12 h, then the obtained spreading cultivation solution was centrifuged to collect wet cells, and the wet cells were washed with inorganic salt medium, thereby obtaining the resting cells of *Stenotrophomonas maltophilia* GYH.

Figure 4:
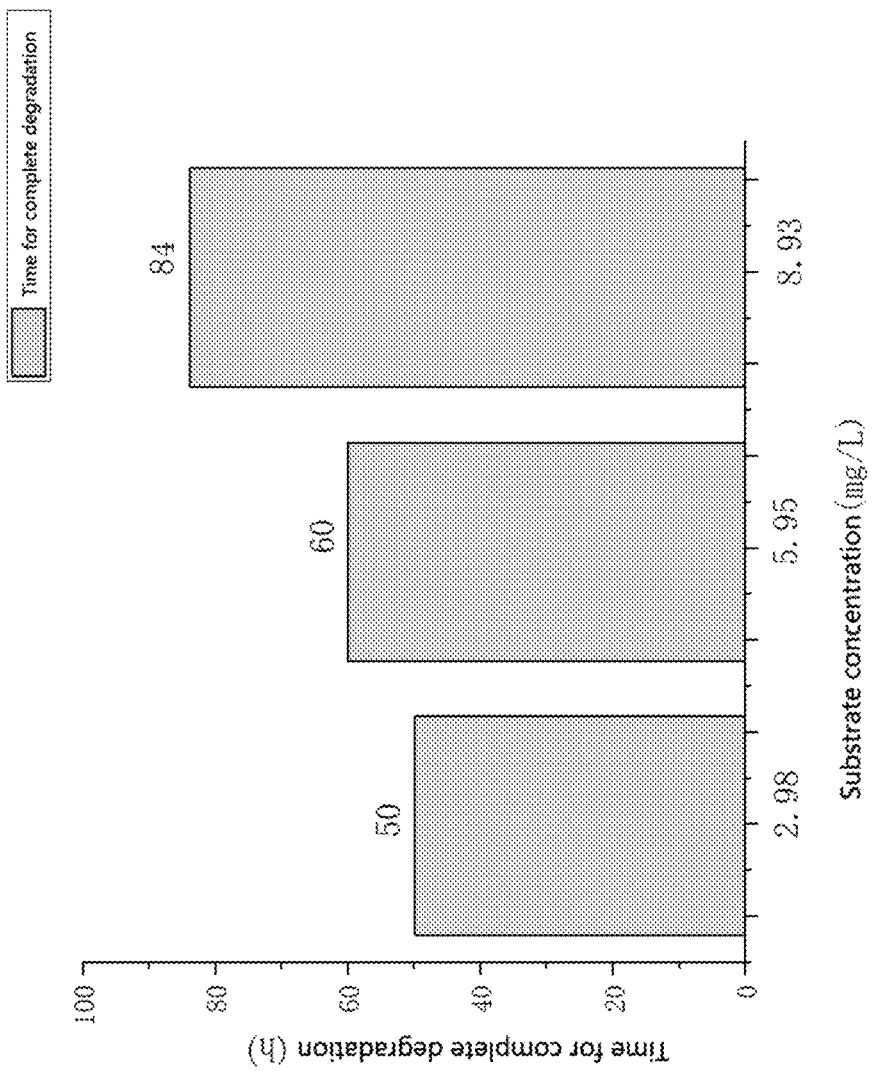
FIG. 4 shows the time required for complete degradation by different concentrations of the strain GYH.
Figure 5:
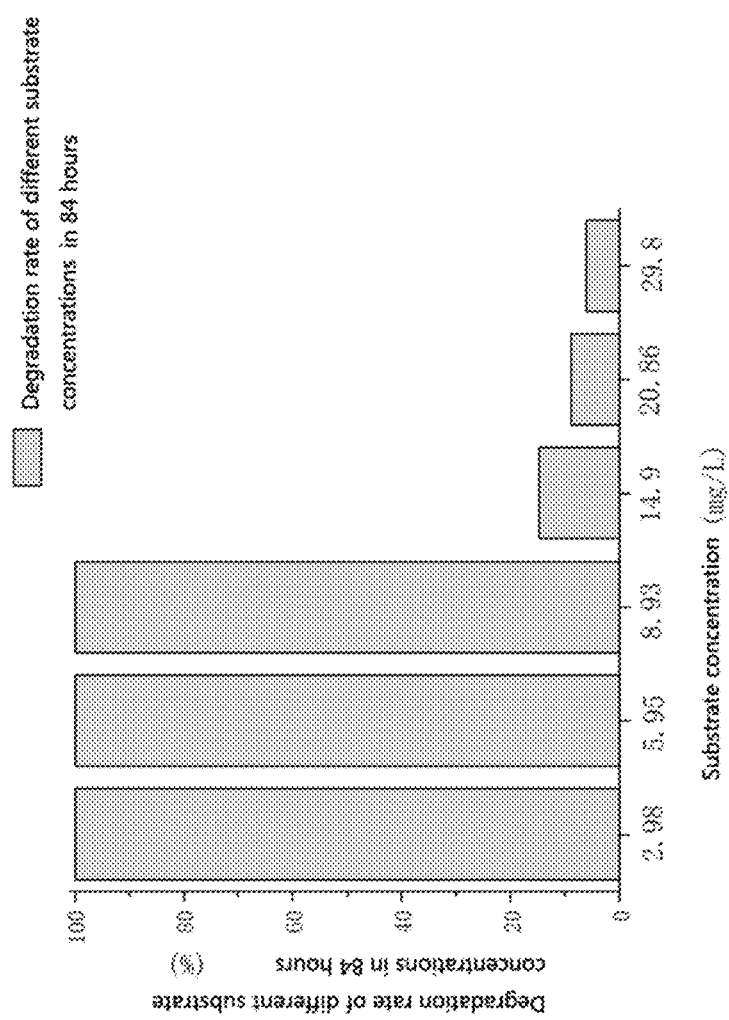
FIG. 5 shows degradation rate of different concentrations of the substrates within 84 h by the strain GYH.

Example 3: Detection of Degradation Performance of *Stenotrophomonas maltophilia* GYH on Chloroform with Different Concentrations Each 50 mL of inorganic salt medium were put into a 330 mL shake flask, and sterilized at 110° C. for 40 min. After sterilization, the inorganic salt mediums were place at room temperature for 2 days to confirm no bacteria growth. Resting cells of *Stenotrophomonas maltophilia* GYH obtained by the method in Example 2 were added with the final concentration of 80 mg/L (calculated by dry cell weight), and then chloroform was added as the only carbon source with the final concentrations of 2.98 mg/L, 5.93 mg/L, 8.93 mg/L, 14.85 mg/L, 20.97 mg/L and 29.8 mg/L respectively, after sealing the shake flask, the resulting solutions were cultured on a shaker at 30° C., 160 rpm, and a blank control without bacteria was taken. The concentration of residual chloroform in the shake flask was determined regularly, and the generation of chloride ions in the solution was determined regularly. Bar graphs of time required for complete degradation of different substrate concentrations and degradation rate under different substrate concentrations within 84 h were drawn. The results were shown in FIG. 4 and FIG. 5. The results showed that when the concentration of chloroform was lower than 8.93 mg/L, the strain GYH could quickly degrade the added substrate.

Example 4: Studies on Broad Spectrum of Substrates of *Stenotrophomonas maltophilia* CCTCC NO: M 20191025

The substrate in Example 3 was changed to that shown in Table 2, and the final concentration of the substrate was 10 mg/L. Other operations were the same as in Example 3. The results were shown in Table 2. It can be seen from Table 2 that *Stenotrophomonas maltophilia* CCTCC NO: M 20191025 has a degrading effect on all the chlorinated hydrocarbon organics. It can completely degrade 10 mg/L of chlorobenzene within 48 hours, can completely degrade 10 mg/L 1.2-dichloroethane within 72 hours, and also has a certain degradation effect on the other three chlorinated hydrocarbons.

TABLE 2

Degradation effects of different substrates

| Substrate (10 mg/L) | Degradation time (h) | Removal rate (%) |
|---|---|---|
| Chlorobenzene | 48 | 100 |
| 1.2-Dichloroethane | 72 | 100 |
| 1.1.1-Trichloroethane | 72 | 82.90 |
| Dichloromethane | 72 | 71.52 |
| Trichloroethylene | 72 | 41.35 |

Figure 6:
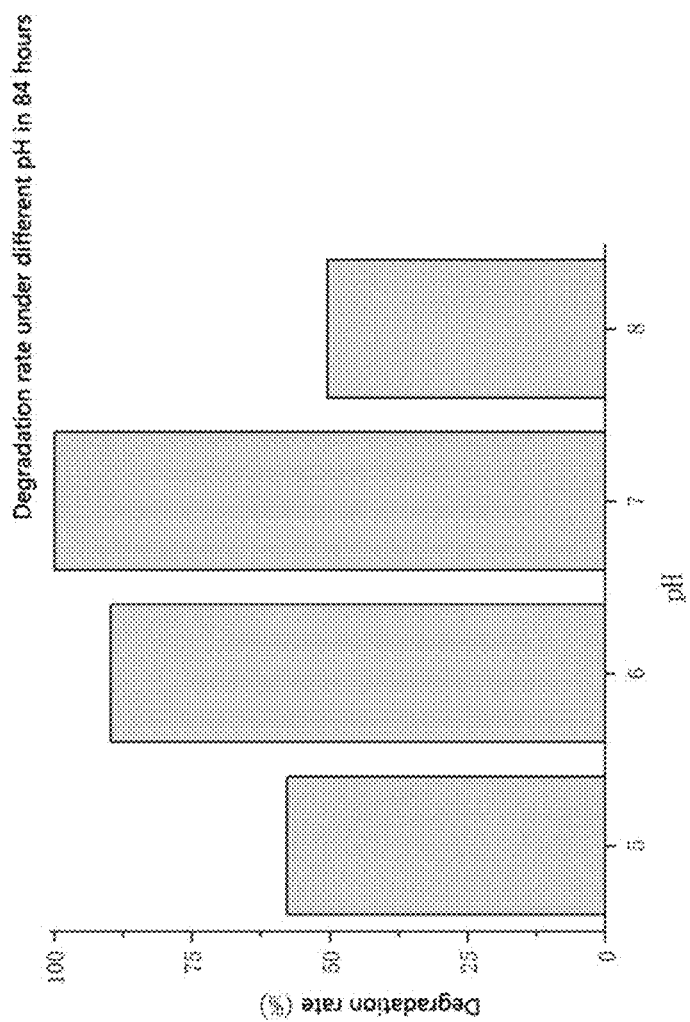
FIG. 6 shows degradation rate at different pH within 84 h by the strain GYH.

Example 5: Degradation Performance Detection of *Stenotrophomonas maltophilia* CCTCC NO: M 20191025 on Chloroform with Different pH Each 50 mL of inorganic salt medium was put into a 330 mL shake flask, and sterilized at 110° C. for 40 min; wherein the pH value of the inorganic salt medium in each shake flask was 5, 6, 7 and 8 respectively. After sterilization, the inorganic salt mediums were placed at room temperature for 2 days to confirm no bacteria growth. The resting cells of *Stenotrophomonas maltophilia* GYH obtained by the method in Example 2 were added with the final concentration of 80 mg/L (calculated by dry cell weight), and then chloroform was added as the only carbon source with the final concentrations of 8.93 mg/L, after sealing the shake flask, the resulting solution was cultured on a shaker at 30° C., 160 rpm, and a blank control without bacteria was taken. The concentration of residual chloroform in the shake flask was determined regularly, and the generation of chloride ions in the solution was determined regularly, thereby obtaining time for complete degradation under different pH. The results were shown in FIG. 6. It showed that the best pH for the strain GYH to degrade chloroform was 7.

Although the present invention has disclosed the above examples, it is not intended to limit the scope of protection of the present invention. Changes and modifications made by any technical person familiar with the technology, without departing from the concept and scope of the present invention, should be involved in the scope of protection of the present invention.

The invention claimed is:

1. A method of degrading a chlorinated hydrocarbon pollutant with *Stenotrophomonas maltophilia* GYH, comprising: adding cells obtained by large-scale cultivation of *Stenotrophomonas maltophilia* GYH to an inorganic salt medium with a pH of 5-8; adding the chlorinated hydrocarbon pollutant; and culturing the cells at 20-35° C. while shaking at 140-180 rpm to degrade the chlorinated hydrocarbon pollutant, wherein the *Stenotrophomonas maltophilia* GYH is preserved in China Center for Type Culture Collection with the preservation number CCTCC NO: M 20191025.

2. The method of claim 1, wherein the chlorinated hydrocarbon pollutant is at least one selected from the group consisting of chloroform, chlorobenzene, 1,2-dichloroethane, 1,1,1-trichloroethane and dichloromethane.

3. The method of claim 1, wherein the dry weight of cells in the inorganic salt medium is 50-100 mg/L.

4. The method of claim 1, wherein the concentration of the chlorinated hydrocarbon pollutant added to the inorganic salt medium is 1-10 mg/L.

5. The method of claim 1, wherein the inorganic salt medium comprises 2 g/L $KH_2PO_4$, 2 g/L $(NH_4)_2SO_4$, 0.025 g/L $MgSO_4$ and 0.18 g/L NaOH in ultrapure water at a pH of 5-8.

6. The method of claim 1, further comprising preparing cells of *Stenotrophomonas maltophilia* GYH by inoculating *Stenotrophomonas maltophilia* GYH onto an LB agar slant medium and culturing at 30° C. in an incubator, thereby obtaining a bacterial slant culture, wherein the LB slant agar medium consists of: 5 g/L yeast extract, 10 g/L NaNO3, 10 g/L peptone and 15-20 g/L agar in deionized water at a neutral pH; and inoculating the slant cells into an LB liquid medium and incubating at 30° C. while shaking at 160 rpm for 12 h to obtain large-scale cultivation solution; centrifuging the solution to collect cells, and washing the cells with the inorganic salt medium to obtain the cells of *Stenotrophomonas maltophilia* GYH, wherein the LB liquid medium contains 5 g/L yeast extract, 10 g/L $NaNO_3$ and 10 g/L peptone in deionized water at a neutral pH.

\* \* \* \* \*

SEQUENCE LISTING

<160> NUMBER OF SEQ ID NOS: 1

<210> SEQ ID NO 1
<211> LENGTH: 1344
<212> TYPE: DNA
<213> ORGANISM: Stenotrophomonas maltophilia

<400> SEQUENCE: 1

```
gagcttgctc cttgggtggc gagtggcgga cgggtgagga atacatcgga atctactctg      60
tcgtggggga taacgtaggg aaacttacgc taataccgca tacgacctac gggtgaaagc     120
aggggatctt cggaccttgc gcgattgaat gagccgatgt cggattagct agttggcggg     180
gtaaaggccc accaaggcga cgatccgtag ctggtctgag aggatgatca gccacactgg     240
aactgagaca cggtccagac tcctacggga ggcagcagtg gggaatattg gacaatgggc     300
gcaagcctga tccagccata ccgcgtgggt gaagaaggcc ttcgggttgt aaagcccttt     360
tgttgggaaa gaaatccaac tggttaatac ccggttggga tgacggtacc caaagaataa     420
gcaccggcta acttcgtgcc agcagccgcg gtaatacgaa gggtgcaagc gttactcgga     480
attactgggc gtaaagcgtg cgtaggtggt tatttaagtc cgttgtgaaa gccctgggct     540
caacctggga actgcagtgg atactggatg actagaatgt ggtagagggt agcggaattc     600
ctggtgtagc agtgaaatgc gtagagatca ggaggaacat ccatggcgaa ggcagctacc     660
tggaccaaca ttgacactga ggcacgaaag cgtggggagc aaacaggatt agataccctg     720
gtagtccacg ccctaaacga tgcgaactgg atgttgggtg caatttggca cgcagtatcg     780
aagctaacgc gttaagttcg ccgcctgggg agtacggtcg caagactgaa actcaaagga     840
attgacgggg gcccgcacaa gcggtggagt atgtggttta attcgatgca acgcgaagaa     900
ccttacctgg ccttgacatg tcgagaactt tccagagatg gattggtgcc ttcgggaact     960
```

```
cgaacacagg tgctgcatgg ctgtcgtcag ctcgtgtcgt gagatgttgg gttaagtccc    1020
gcaacgagcg caacccttgt ccttagttgc cagcacgtaa tggtgggaac tctaaggaga    1080
ccgccggtga caaaccggag gaaggtgggg atgacgtcaa gtcatcatgg cccttacggc    1140
cagggctaca cacgtactac aatggtaggg acagagggct gcaagccggc gacggtaagc    1200
caatcccaga aaccctatct cagtccggat tggagtctgc aactcgactc catgaagtcg    1260
gaatcgctag taatcgcaga tcagcattgc tgcggtgaat acgttcccgg gccttgtaca    1320
caccgcccgt cacaccatgg gagt                                           1344
```